United States Patent [19]

Hummelen et al.

[11] Patent Number: 4,705,847

[45] Date of Patent: Nov. 10, 1987

[54] POLYCYCLOALKYLIDENE-POLYCYCLOALKANES, EPIDIOXY DERIVATIVES THEREOF AND METHOD OF PREPARATION

[75] Inventors: Jan C. Hummelen, Groningen; Egbert W. Meijer, Waalre-Aalst; Hans Wynberg, Haren, all of Netherlands

[73] Assignee: Akzo N.V., Arnhem, Netherlands

[21] Appl. No.: 568,224

[22] PCT Filed: Apr. 7, 1983

[86] PCT No.: PCT/NL83/00014

§ 371 Date: Dec. 7, 1983

§ 102(e) Date: Dec. 7, 1983

[87] PCT Pub. No.: WO83/03604

PCT Pub. Date: Oct. 27, 1983

[30] Foreign Application Priority Data

Apr. 7, 1982 [NL] Netherlands .................. 8201492

[51] Int. Cl.$^4$ .................. C07D 9/00; C07D 321/00; C07C 23/38

[52] U.S. Cl. .................. 530/350; 585/352; 585/22; 568/719; 570/183

[58] Field of Search .................. 260/112 R, 112 B; 568/719; 570/183; 585/21, 22, 352; 424/177; 514/2, 510, 511; 530/350

[56] References Cited

U.S. PATENT DOCUMENTS

| | | | |
|---|---|---|---|
| 3,707,576 | 12/1972 | Moore | 585/352 |
| 3,897,479 | 7/1975 | Inamoto et al. | 585/352 |
| 4,008,251 | 2/1977 | Moore et al. | 585/352 |
| 4,043,927 | 8/1977 | Duling et al. | 585/22 |

OTHER PUBLICATIONS

Müller et al, *Methoden der Organishen Chemie*, Band V/4, 1960, Verlag Publishers, pp. 23, 24 & 30.
Müller et al, *Methoden der Organishen Chemie*, Band V/3, 1962, Verlag Publishers, pp. 765, 780, 800.
Wierenga et al, "Tetrahedron Letters", No. 52, pp. 4579–4582, 1980, Pergamon Press.
Wierenga et al, "Tetrahedron Letters", No. 2, pp. 169–172, 1972, Pergamon Press.

*Primary Examiner*—John Kight
*Assistant Examiner*—Nathan M. Nutter
*Attorney, Agent, or Firm*—William M. Blackstone

[57] ABSTRACT

The invention relates to a process for preparing substituted polycyclo-alkylidene polycyclo-alkanes, such as substituted adamantylidene adamantanes, and the corresponding epidioxy compounds, in which polycycloalkylidene polycyclo-alkanes are halogenated with an N-halosuccinimide, tert.-butylhypohalite or sodium hypohalite/CH$_3$COOH, the halogenation product is optionally subjected to a substitution reaction, and the substituted polycycloalkylidene polycyclo-alkanes are converted to the corresponding epidioxy compounds in a way known per se.

Further, the invention relates to compounds of formula 44 in which A and B represent alkylene radicals, which alkylene radicals may be attached to each other via an alkylene radical C, and R$_1$ represents a substituent, which, in case of 4-eq.-R$_1$-2,2'-adamantylidene adamantane cannot be chloro, hydroxy, oxo, D or a group of formula 1:

as well as to compounds of formula 45:

(Abstract continued on next page.)

in which A, B and C are as defined above, and R$_2$ is a substituent which, in case of 4-eq.-R$_2$-2,2'-epidioxy-2,2'-adamantyl adamantane cannot be chloro or hydroxy.

Compounds of formula 45 are useful as thermochemiluminescent labels and probes in the study of biological processes and in immuno-assays.

34 Claims, 47 Drawing Figures

POLYCYCLOALKYLIDENE-POLYCYCLOALKANES, EPIDIOXY DERIVATIVES THEREOF AND METHOD OF PREPARATION

BACKGROUND OF THE INVENTION

A process for preparing substituted polycyclo-alkylidene polycyclo-alkanes and the corresponding epidioxy compounds; as well as said substituted polycyclo-alkylidene polycyclo-alkanes and the corresponding epidioxy compounds.

The invention relates to a process for preparing substituted polycyclo-alkylidene polycyclo-alkanes and the corresponding epidioxy compounds, as well as to these substituted polycycloalkylidene polycyclo-alkanes and the corresponding epidioxy compounds.

Figure 1:
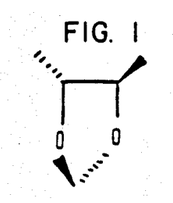
FIG. 1 illustrates a dioxazole radical which can be a substituent in some of the compounds of this invention.
Figure 44:
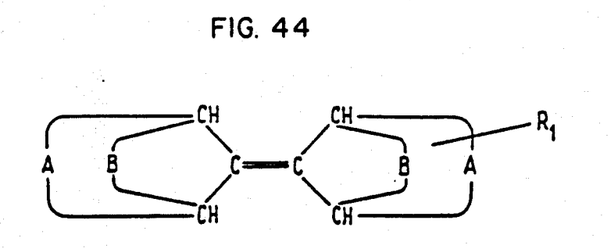
FIG. 44 illustrates the structural formula of the substituted adamantylideneadamantane compounds of the invention.

The term "substituted polycyclo-alkylidene polycyclo-alkanes" as used herein comprises especially compounds of formula 44 of the formula sheet, in which A and B represent alkylene radicals, which alkylene radicals may be attached to each other via an alkylene radical C, and wherein $R_1$ represents a substituent which, in the case of 4-equatorially $R_1$-substituted 2.2'-adamantylidene adamantanes, cannot be chloro, hydroxy, oxo, D or a radical of formula 1 of the formula sheet. In preferred compounds of formula 44, alkylene radical A contains 2 to 5 carbo atoms, alkylene radical B 2 to 5 carbon atoms, and alkylene radical C, if present, 1 to 4 carbon atoms. Examples of compounds of formula 44 are 4-eq-$R_1$-2,2'-adamantylidene adamantanes, 4-eq-$R_1$-9,9'-bicyclo [3,3,1]-nonylidene-bicyclo[3,3,1]-nonanes, 2- or 7-$R_1$-8,8'-bicyclo[3,2,1]-octylidene-bicyclo[3,2,1]-octanes and 2- or 7-$R_1$-10,10'-bicyclo[4,3,1]-decylidene-bicyclo[4,3,1]-decanes, in which the two rings of each of the bicyclic radicals may be attached to each other via an alkylene bridge.

Figure 45:
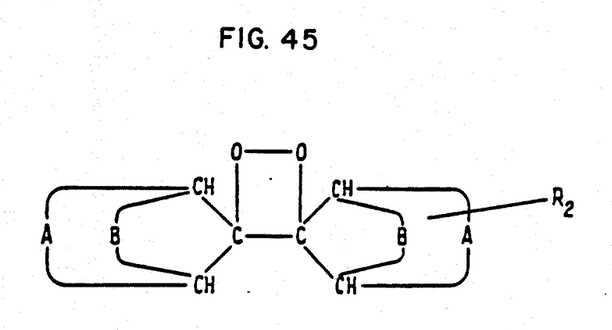
FIG. 45 illustrates the structural formula of the 2,2'-epidioxy derivatives of the substituted adamantylideneadamantane compounds of the invention.

The corresponding epidioxy compounds—which contain a dioxetane ring—are especially compounds of formula 45, in which A, B and C, if present, have the above-mentioned meanings, and $R_2$ represents a substituent which, in the case of 4-eq-$R_2$-2,2'-epidioxy-2,2'-adamantyl adamantane cannot be chloro or hydroxy.

The invention relates to these compounds and to processes for the preparation thereof. Especially, the invention relates to a process for preparing substituted polycyclo-alkylidene polycyclo-alkanes, in which a corresponding non-substituted compound is subjected to a halogenation reaction, using a halogenating agent in a solvent, and the halogenation product is recovered from the reaction mixture and/or, if desired, is subjected to a substitution reaction.

In Tetrahedron Letters 1970, 4579-82, J. H. Wieringa, J. Strating and H. Wynberg describe a process in which adamantylidene adamantane is reacted with chlorine is tetrachloromethane at a temperature of −20° to +10° C. to form 4-eq.-chloroadamantylidene adamantane in addition to polychlorinated products. The chloro-substituted adamantane compound is the starting point for further reaction in the presence of $AgNO_3$ and $THF/H_2O$ to form a mixture of the corresponding 4-hydroxy-adamantylidene adamantane compounds, which with the appropriate oxidant (Jones reagent: $CrO_3$, $H_2SO_4$, acetone) are finally converted into the corresponding ketone compound, in which the carbonyl group is in the 4-position.

SUMMARY OF THE INVENTION

It is an object of the invention to provide a process for preparing substituted polycyclo-alkylidene polycyclo-alkane compounds, in which these compounds are selectively produced in a high yield and in a simple manner and/or from which other substituted polycyclo-alkylidene polycyclo-alkane compounds can be selectively prepared in a high yield.

According to the invention, for this purpose, the process as defined above is carried out using as the halogenating agent N-halosuccinimide, tert-butylhypohalite, or sodium hypohalite/$CH_3COOH$.

The invention is based on the surprising discovery that, with the halogenating agents mentioned, polycyclo-alkylidene polycyclo-alkanes which can be considered to be tetra-alkyl ethylene compounds, such as the adamantylidene adamantane, produce halogenation products with a structure, namely, the 4-eq.-halogen-substituted structure, which differs from the structure normally to be expected in reactions of these halogenating agents with mono-, di- and trialkylethylene compounds. Thus, in the process according to the invention, halogenation of the adamantylidene adamantane by means of N-chlorosuccinimide in boiling $CCl_4$ and in the presence of a radical initiator exclusively produces the 4-eq.-chloro-substituted compound. This halogenation reaction, carried out in $CH_2Cl_2$ at room temperature and in the absence of a radical initiator, produces the 4-eq.-chloro-substituted compound in a quantitative yield in a smoothly proceeding reaction. The halogenation reaction also takes place in $CCl_4$, $CHCl_3$, or in a mixture of $CH_2Cl_2/CH_3COOH$, with the reaction velocity increasing with increasing polarity of the solvent.

It has been found that, in the presence of a radical inhibitor, for example hydroquinone, the halogenation reaction takes place at a high rate.

A further elaboration of the process according to the invention concerns causing the chlorine atom in the chloro-substituted compound formed to participate in a substitution reaction in a solvent in the presence of a silver salt, using as the substituting agent, in addition to the silver salt, a nucleophile, for example, an alcohol, a cyanide, a carbamate, or an isothiocyanate.

When, for example, 4-eq.-chloroadamantylidene adamantane is dissolved in an alcohol or a mixture of the alcohol and dioxane and $AgBF_4$ is added, a fast proceeding reaction takes place, in which the corresponding ether is formed without appreciable quantities of byproduct. In this reaction, the reaction components may be directly mixed with each other, whereby they react at room temperature or at a slightly elevated temperature. The degree of selectivity of the formation of a given ether is promoted by a careful preparation of the reaction components in the sense that they should be thoroughly dry.

In the reaction of 4-eq.-chloroadamantylidene adamantane with certain alcohols, for example, methanol, n-octanol-1 and hydroxy-acetone, these alcohols may themselves serve as the solvent, and hence be used in large excess. It has been found, however, that the yield of product ether did not decrease dramatically when a lower concentration of the alcohol component in the reaction mixture is selected.

When 4-eq.-chloroadamantylidene admantane is reacted with a nitrile as the nucleophile in the presence of $AgBF_4$, taking care that the imminium ions formed are hydrolysed with water, there is produced N-(4-eq.-adamantylidene adamantyl)amide, albeit that, generally speaking, these reactions with a nitrile proceed at a lower rate than with alcohols while the yield is also comparatively lower.

The reaction of, in particular, 4-eq.-chloroadamantylidene adamantane with alcohols to form ethers and with nitriles to form amides are the first steps on a route leading to diverse 4-eq.-substituted adamantylidene adamantanes, and via these compounds to the corresponding 1,2-dioxetanes, which will be entered into later.

In a preferred embodiment of the process according to the invention, the halogenating agent is a brominating agent, for example, N-bromosuccinimide, and, in accordance with the above, there is then produced the 4-eq.-bromo-substituted compound. When the starting point is, for example, the adamantylidene adamantane, heating for 12 hours at 40° C. produces 4-eq.-bromoadamantylidene adamantane according to a fully completed reaction.

The 4-eq.-bromoadamantylidene adamantane has bee found to have particularly advantageous and unexpected properties. Thus, unlike the corresponding 4-eq.-chloroadamantylidene adamantane, this compound permits carrying out substitution reactions by means of solvolysis without requiring an adjuvant such as an $Ag^+$ salt. It has moreover been found that certain substituents can be introduced in one step where this had not been possible before. The 4-eq.-bromoadamantylidene adamantane reacts with primary and secondary alcohols to form ethers, with carboxylic acids to form esters, with primary amines to form secondary amines, and with nitriles to form N-adamantylidene adamantyl amides. Furthermore it has been found to be possible to carry out halogen exchange reactions with this compound, for example, in a reaction with NaI/acetone. Reaction of 4-eq.-bromoadamantylidene adamantane with H$_2$O/dioxane gives a quantitative yield of 4-eq.-hydroxyadamantylidene adamantane. The solvolysis reactions are carried out in the pure reagent as the solvent or together with dioxane or DMF as a co-solvent.

According to another elaboration of the process according to the invention, the symmetrical polycycloalkylidene polycycloalkane used as the starting point is adamantylidene adamantane. Preferably the 4-eq.-substituted adamantylidene adamantane is subjected to a photo-oxigenation reaction to form the 4-eq.-substituted 1,2-dioxetane, as 1,2-dioxetanes have particularly advantageous properties, as will be explained in more detail hereinafter.

DETAILED DESCRIPTION OF THE INVENTION AND PREFERRED EMBODIMENTS

The invention also relates to substituted polycycloalkylidene polycycloalkanes, especially to compounds of formula 44 as defined above, and preferably to 4-eq.-R$_1$-substituted adamantylidene adamantane compounds, and in particular those in which R$_1$ is bromine, with the exception of the known per se 4-eq.-R$_1$-substitutedadamantylidene adamantanes in which R is chlorine, hydroxyl, oxo, D or a group having the formula 1 of the sheet of formulae. A favourable property of adamantylidene adamantanes in general is that the 1,2-dioxetanes produced from them exhibit a good stability, as appears from a summary of a so-called "poster session" on bio- and chemiluminescence, published in June 1981 by Academic Press, New York.

1,2-dioxetanes themselves are stated in an article by T. Wilson in Int. Rev. Sci.: Phys. Chem. Ser. Two 9 (1976) 265 to be suitable as thermochemiluminescent compounds, with the possibility of controlling the chemiluminescence emitted by regulating the temperature of the system.

In accordance with the above, the invention accordingly also relates to chemiluminescent compounds of formula 45, in which A and B represent alkylene radicals, which alkylene radicals may be attached to each other via an alkylene radical C, and wherein R$_2$ represents a substituent which, in the case of 4-eq.-R$_2$-2,2'-epidioxy-2,2'-adamantyl adamantane cannot be chloro or hydroxy.

In preferred compounds of formula 45 the alkylene radical A contains 2 to 5 carbon atoms, the alkylene radical B 2 to 5 carbon atoms, and the alkylene radical C, if present, 1 to 4 carbon atoms. In particular, the invention relates to 4-eq.-R$_2$-2,2'-epidioxy-2,2'-adamantyl adamantanes in which R$_2$ represents a substituent, with the exception of chloro or hydroxy.

For example, the substituent R$_2$ may be chloro, bromo or iodo, a hydroxy group, an optionally substituted alkoxy, cycloalkoxy or acyloxy group, or an amino, acylamino, isothiocyanato or isocyanato group, with the proviso that in case of 4-eq.-R$_2$-2,2'-epidioxy-2,2'-adamantyl adamantane R$_2$ cannot be chloro or hydroxy.

In particular, the substituent R$_2$ represents a radical of a biologically active compound, such as of a fatty acid, a steroid, or a protein. In that case the compound of formula 45 is a biologically active substance labelled with a chemiluminescent 1,2-dioxetane.

It is true that is known, within the framework of the analytical techniques used in biochemistry, clinical chemistry and biology for the qualitative and quantitative analysis and structural assay of biological materials to use luminescent labels and probes. The compounds have chemiluminescent properties, such as luminol and other phthalohydrazide derivatives used in these techniques, however, have the limitation that their chemiluminescence can only be generated by adding oxidants, for example hydrogen peroxide.

The novel chemiluminescent labels according to the present invention are suitable for use in immunochemical methods of determination, in particular immunoassay, and the study of steroids and membranes. Unlike known agents, such as luminol, the chemiluminescence is generated solely by heating.

To study, in particular, membranes, the thermochemiluminescent compounds according to the invention are modified to a label which exhibits chemiluminescence at a temperature of at least 150° C. and up to approximately 250° C. By suitable substitution of the 1,2-dioxetane according to the invention, for example, by a long-chain fatty acid, the label is rendered compatible with the surroundings to be studied at the membrane.

Figure 28:
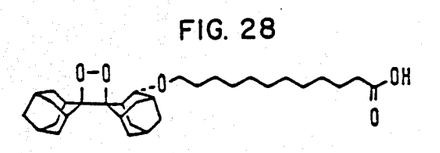

A thermochemiluminescent fatty acid compound according to the invention is, for example, the compound of formula 28, in which the fatty acid radical is derived from arachidic acid. Such a compound has been found to have properties analogous to those of long-chain fatty acids, and to be suitable for use as a chemiluminescent label in membrane studies.

For chemiluminescence immunoassay based on a specific antibody-antigen reaction, a dioxetane compound according to the invention is modified to a "label", for example a protein label which is specific relative to certain functional groups in peptides.

Figure 29:
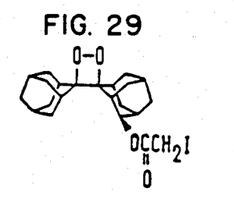
FIG. 29 illustrates 4-eq.-(alpha-iodoacetoxy)-2,2'-epidioxy-2,2'-adamantyladamantane (anti-isomer) of the invention.
Figure 30:
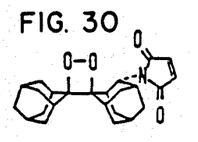
Figures 33, 34, 35, 36, 37, 38, 39, 40, 41, 42A, 42B, 43:
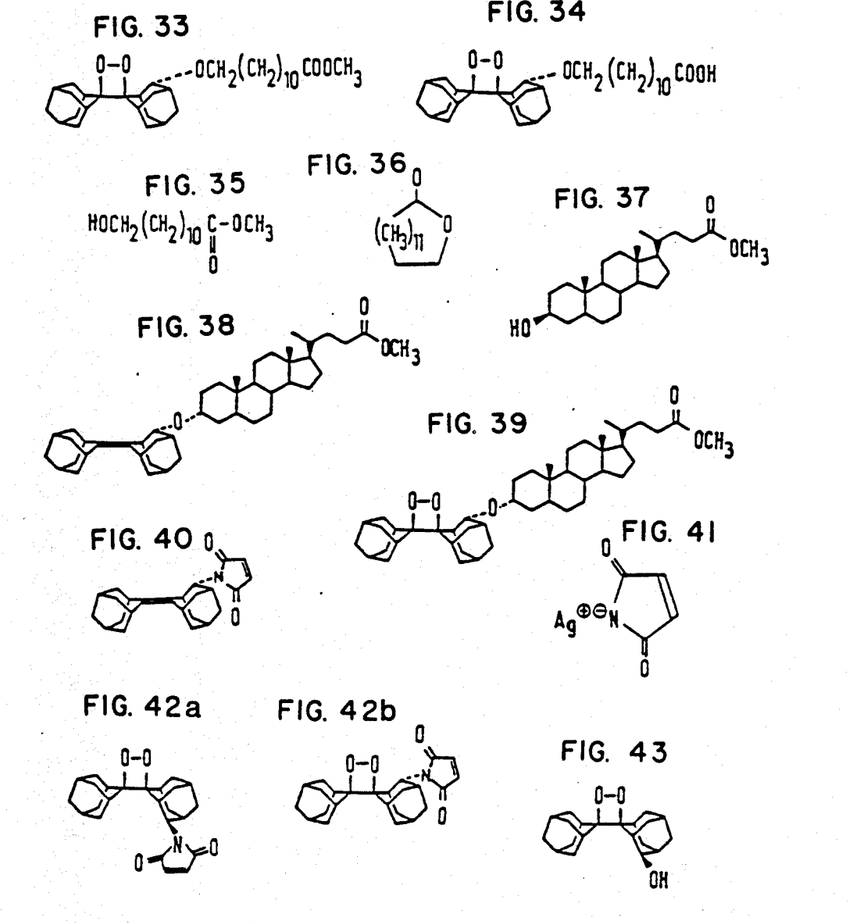
FIG. 33 illustrates the structural formula of 4-eq.-[12-oxydodecanoic acid methyl ester]adamantylideneadamantane-1,2-dioxetane.
FIG. 34 illustrates the structural formula of 4-eq.-[12-oxydodecanoic acid]adamantylideneadamantane-1,2-dioxetane.
FIG. 35 illustrates the structural formula of 12-hydrdoxydodecanoic acid methyl ester.
FIG. 36 illustrates the structural formula of dodecane lactone.
FIG. 37 illustrates the structural formula of lithocholic acid methyl ester.
FIG. 38 illustrates the structural formula of 3-O-(4-eq.-adamantylideneadamantyl)lithocholic acid methyl ester.
FIG. 39 illustrates the structural formula of 3-O-(4-eq.-2,2'-epidioxy 2,2'-adamantyladamantane)lithocholic acid methyl ester.
FIG. 40 illustrates the structural formula of N-(4-eq.-adamantylideneadamantyl)maleimide.
FIG. 41 illustrates the structural formula of silver maleimide.
FIG. 42a illustrates the structural formula of an isomer of 4-eq.-(maleimido)-2,2'-epidioxy-2,2'-adamantyladamantane
FIG. 42b illustrates the structural formula of an isomer of 4-eq.-(maleimido)-2,2'-epidioxy-2,2'-adamantyladamantane.
FIG. 43 illustrates the structural formula of 4-eq.-hydroxy-2,2'-epidioxyadamantylideneadamantane.

Thus, for example, a protein may be marked at a free thiol group with a 4-eq.-substituted 2,2'-epidioxy-2,2'-adamantyl adamantane in which the substituent is α-iodoacetoxy of maleimido (formulae 29 and 42, respectively, of the sheet of formulae). The 1,2-dioxetane thus substituted may be reacted under standard conditions with, for example, Bovine Serum Albumine, which is a protein having 0.7 mole of free thio groups per mole of protein. Purification of the reaction product by chromatography over a Sephadex G-10 column, dialysis against distilled water, and freeze drying produces the chemiluminescent protein. This procedure may also be applied to other proteins and, for example, to glutathione.

Figures 21, 22, 23, 24, 25, 26, 27:
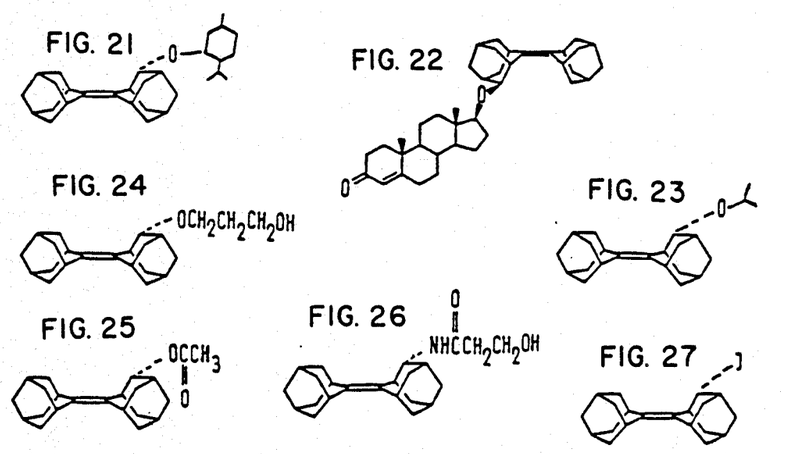
FIG. 21 illustrates the structural formula of 4-eq.-(L)-menthoxyadamantylideneadamantane.
FIG. 22 illustrates the structural formula of 17-beta-[4-eq.-adamantylideneadamantyloxy]testosterone.
FIG. 23 illustrates the structural formula of 4-eq.-(isopropyloxy)adamantylideneadamantane.
FIG. 24 illustrates the structural formula of 4-eq.-(3-hydroxypropyloxy)adamantylideneadamantane.
FIG. 25 illustrates the structural formula of 4-eq.-acetoxy-adamantylideneadamantane.
FIG. 26 illustrates the structural formula of N-(4-eq.-adamantylidene adamantyl)-3-hydroxypropionamide.
FIG. 27 illustrates the structural formula of 4-eq.-iodoadamantylideneadamantane.
Figure 31:
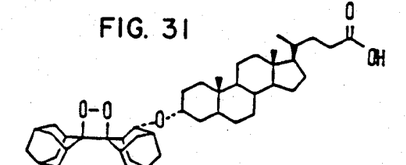
FIG. 31 illustrates 3-O-(4-eq.-2,2'-epidioxy-2,2'-adamantyladamantane)lithocholic acid of the invention.

For immunoassay on the basis of chemiluminescence for steroid investigation, the 1,2-dioxetane compound according to the invention may be attached to, for example, lithocholic acid (formula 31) or testosterone (formula 22).

The invention is illustrated in and by the following examples.

EXAMPLE I

In the examples, melting points were determined by means of a Mettler FP2 melting point apparatus. IR spectra were recorded with a Unicam (SP-200) spectrophotometer and $^1$H NMR spectra with a Varian A-60 of Hitachi Perkin Elmer R-24 B at 60 Mc. $^1$H chemical shifts are given in δ units (ppm) relative to TMS (tetramethylsilane).

$^{13}$CMR spectra were recorded at 25 Mc (Varian XL-100) and $^{13}$C chemical shifts are indicated in δ units (ppm) relative to the solvent CDCl$_3$ and converted to δ TMS values using δD KCl$_3$=76.9 ppm.

Mass spectra were recorded by means of a Perkin Elmer Polarimeter using a 10 cm cell.

All solvents were purified and dried according to standard conditions. Silvers salts (AgBF$_4$; AgClO$_4$) were dried with P$_2$O$_5$ at 0.001 mm Hg for 10–20 hours.

Figure 2:
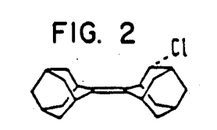
FIG. 2 illustrates the structural formula of 4-eq.-chloroadamantylideneadamantane.

The 4-eq.-chloroadamantylidene adamantane (formula 2 of the sheet of formulae) used in the examples can be characterized as follows: melting point 142°–143° C. $^{13}$C NMR (CDCl$_3$): 137.0; 130.8; 68.3; 39.4; 39.2; 38.8; 37.0; 35.6; 32.4; 32.1; 30.4; 30.4; 28.3; 27.6.

Figure 3:
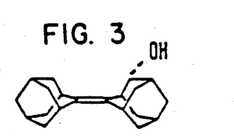
FIG. 3 illustrates the structural formula of 4-eq.-hydroxyadamantylideneadamantane.
Figure 4A:
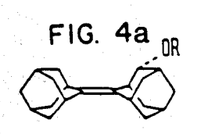
FIG. 4a illustrates the structural formula of a 4-eq.-4'-eq.-bisadamantylidene adamantyl ether when R is the radical of FIG. 4b.
Figure 4B:
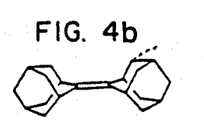
FIG. 4b illustrates the structural formula of a 4-eq adamantylideneadamantyl radical.

Preparation of 4-eq.-hydroxyadamantylidene adamantane (formula 3) and 4-eq.-, 4′-eq.-bisadamantylidene adamantyl ether (formula 4a in which R represents a group having formula 4b)

4-eq.-chloroadamentylidene adamantane having formula 2 (12.8 g; 40 mmoles) was dissolved in dioxane (160 cm$^3$) and distilled water (40 cm$^3$) was added. The mixtures was refluxed, and with stirring, AgBF$_4$ (10 g, 50 mmoles) was added in small quantities together with 120 cm$^3$ dioxane over a period of 75 minutes. Refluxing was continued for 15 minutes, whereafter the reaction mixture was cooled, filtered and concentrated. The residue was taken up in ether (120 cm$^3$), the ethereal solution was washed with water (3×100 cm$^3$), dried with MgSO$_4$, decolourized with 1 g activated charcoal, filtered and evaporated to yield 11.09 (97%) of the compound having formula 3 in the form of a white powder having a melting point of 211.5°–213° C.

When the reaction was carried out in a dioxane/water (25/1) mixture and AgBF$_4$ was added all at once, after work-up and chromatography over Al$_2$O$_3$ (act. II/III) using CH$_2$Cl$_2$ as the eluent, the compound having formula 4a, in which R represents the group having formula 4b, cound be isolated in a yield of 25%. Even after recrystallization (from n-hexane) a sharp melting point could not be obtained, probably because the compound having formula 4a consisted of a mixture of diastereo-isomers. $^1$H NMR (CDCl$_3$) δ 3.33 (br, 2H); 3.05–2.55 (m, 8H); 2.50–1.1 (m, 44H). $^{13}$C NMR (CDl$_3$): δ 135.2; 135.1; 131.6; 131.4; 80.7; 39.7; 39.5; 39.2; 37.2; 33.4; 32.3; 32.1; 31.4; 31.0; 28.5; 27.8: IR (KBr) 2900 (s), 1455 (m), 1080 (s), 1035 (m) and 975 (m) cm$^{-1}$. Mass: M+ at m/e 550 (30%), 267 (100%) with metastable peak at 129.6. Exact mass: calculated for C$_{40}$H$_{54}$O: 550.417. Found 550.418.

EXAMPLE II

Figure 5:
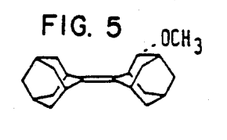
FIG. 5 illustrates the structural formula of 4-eq.-methoxyadamantylideneadamantane.

Preparation of 4-eq.-methoxyadamantylidene adamantane (formula 5)

The chloro-substituted compound having formula 2 (605 mg, 2 mmoles) was suspended in very dry MeOH (10 cm$^3$) under a nitrogen atmosphere and using a magnetic stirrer. Subsequently 600 mg (3 mmoles) AgBF$_4$ was added and the mixture was refluxed for 30 min. AgCl was filtered off and Et$_2$O (50 cm$^3$) was added. The solution was washed with H$_2$O (2×100 cm$^3$), dried with MgSO$_4$, filtered and concentrated at a reduced pressure to produce 520 mg (88%) spectroscopically pure compound having formula 5 in the form of a colourless oil. "Kugelrohr" distillation (170°–180°/0.1 mm Hg) yielded 500 mg analytically pure material which solidified on standing: $^1$H NMR (CDCl$_3$): δ 3.3 (br, 1H); δ 3.3–2.6 (br-5H); δ 2.3–2.1 (br, 22H). $^{13}$C NMR (CDCl$_3$): 135.3, 130.8; 83.3; 54.9; 39.3; 39.0; 37.0; 36.7; 35.1; 32.6; 32.2; 31.8; 31.0; 30.8; 28.3; 24.5. Mass: M+ at m/e 298 (100). IR (neat) 2900, 1450 and 1095 cm$^{-1}$. Analysis: calculated for C$_{21}$H$_{30}$O: 84.51, C; 10.13, H. Found: 84.81. C; 10.05, H.

EXAMPLE III

Figure 6:
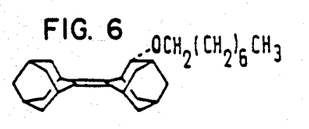
FIG. 6 illustrates the structural formula of 4-eq.-n-octyloxyadamantylideneadamantane.

Preparation of 4-eq.-n-octyl-oxy-adamantylidene adamantane (formula 6)

The chloro-substituted compound having formula 2 (605 mg, 2 mmoles) was suspended in n-octanol-1 (5 cm$^3$). With stirring by means of a magnetic stirrer, AgBF$_4$ (600 mg, 3 mmoles) was added in 2 portions. The mixture was heated for 5 minutes at 100° C. and then allowed to cool to room temperature while it was stirred for 3 hours. Ether (75 cm$^3$) was added and the solution was washed with water (2×100 cm$^3$), dried with MgSO$_4$, filtered and evaporated at 0.3 mm/100° C. Column chromatography over Al$_2$O$_3$ (act. II/III) using CH$_2$Cl$_2$ as the eluent produced 640 mg (81%) spectroscopically pure compound having formula 6 in the form of a colourless oil. $^1$H-NMR (CDCl$_3$) δ 3.55–3.10 (3H, m); δ 3.10–2.60 (4H, m); δ 2.33–0.6 (37H). —C NMR (CDCl$_3$): δ 135.1; 131.2; 81.6; 67.3; 39.4; 39.1; 37.1; 36.8; 35.6; 32.9; 32.3; 31.9; 31.7; 31.0; 30.2; 29.4; 29.1; 28.4; 27.6; 26.2; 22.5; 13.8. Mass: M+ at m/e 396, 267, 266, 41 (100%). Exact mass: calculated for C$_{28}$H$_{44}$O: 396,339. Found: 396,342.

EXAMPLE IV

Figure 7:
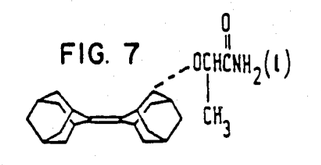
FIG. 7 illustrates the structural formula of O-(4-eq.-adamantylideneadamandyl)lactamide.

Preparation of O-(4-eq.-adamantylidene adamantyl)lactamide (formula 7)

To a solution of 2.0 g l-lactamide (Merck) and 605 mg (2 mmoles) of chloro-substituted compound having formula 2 in 15 cm$^3$ dioxane, AgBF$_4$ (4 mmoles) was added with vigorous stirring at 70° C. The mixture was stirred at room temperature for 20 hours, diluted with ether (150 cm$^3$), washed with water, dried with MgSO$_4$, filtered and concentrated to produce 600 mg of a white material. Column chromatography using Al$_2$O$_3$/CH$_2$Cl$_2$ gave 200 mg non-reacted compound having formula 2 and then 330 mg of the compound having formula 7 (70%, based on converted compound having formula 2), which solidified when stripped with ether; melting point 133°–135° C. $^1$H-NMR (CDCl$_3$) 6.4 (br, 2H); 3.88 (q, J=6.5 c.; 1H); δ 3.32 (m, 1H); δ 2.80 (m, 4H); 2.3–1.1 (m, 25H) with doublet at 1.39, J=6.5 Hz. $^{13}$C-NMR (CDCl$_3$): δ 177.4; 135.9; 130.0; 81.1; 80.8; 73.1 (br); 39.2; 38.6; 36.8; 36.5; 35.8; 32.8; 32.1; 31.8; 30.9; 30.5; 28.1; 27.2; 18.8; 18.5. IR (KBr): 3460, 3300, 2900, 1670, 1580, 1450, 1100, 1060 cm$^{-1}$. Mass: m+ at m/e 355, 267, 137, 91. Exact mass: calculated for C$_{23}$H$_{33}$NO$_2$ 355.251. Found: 355.253.

EXAMPLE V

Figure 8:
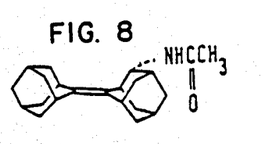
FIG. 8 illustrates the structural formula of N-(4-eq.-adamantylideneadamantyl)acetamide.

Preparation of N(4-eq.-adamantylidene adamantyl)-acetamide (formula 8)

A solution of 1.21 (4 mmoles) of the compound having formula 2 in 20 cm$^3$ dry dioxane was added to a stirred solution of 1.2 g AgBF$_4$ in 20 cm$^3$ CH$_3$CN and 20 cm$^3$ dioxane in a period of 5 minutes and at reflux temperature. After completion of the addition, the whole was stirred for 1 hour and a half without further heating. Water (2 cm$^3$) was added and after stirring for 5 minutes the mixture was concentrated at a reduced pressure. To the residue, 300 cm³ ether was added and after filtration over a glass filter, the ethereal solution was washed with water (3×300 cm³), dried with MgSO₄, filtered and concentrated to produce 1.11 g of the crude compound having formula 8 in the form of a white foam. Column chromatography over Cl₂O₃, using first hexane (150 cm³) and then CH₂Cl₂ as eluents produced 0.86 g (66%) pure acetamide in the form of white crystals; melting point 159°–161° C. (from hexane). $^1$H-NMR (CDCl₃): δ 5.75 (br, 1H); 3.9 (br, 1H); 2.88 (m, 4H); 2.4–1.3 (m, 25H, with peak for —CH₃ at 2.00). $^{13}$C-NMR (CDCl₃): δ 169.0; 135.8; 130.5; 53.9; 39.3; 39.0; 38.8; 37.6; 37.1; 35.3; 33.2; 32.0; 31.7; 31.3; 30.6; 28.3; 28.2; 27.3; 23.5. IR (KBr) 3400, 2950, 1650, 1550, 1460 and 1090 cm$^{-1}$. Mass: M⁺ at m/e 325, 213, 135, 79, 41. Exact mass: calculated for $C_{22}H_{31}NO$: 325.241. Found 325.240.

EXAMPLE VI

Figure 9:
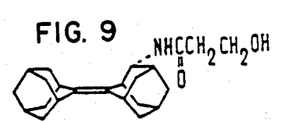
FIG. 9 illustrates the structural formula of N-(4-eq.-adamantylideneadamantyl)-3-hydroxypropionamide.

Preparation of N-(4-eq.-adamantylidene adamantyl)-3-hydroxypropionamide (formula 9)

The chloro-substituted compound having formula 2 (605 mg, 2 mmoles), 3-hydroxypropionitrile (10 cm³) and dioxane (50 cm³) were mixed together under a nitrogen atmosphere at 70° C. to produce a homogeneous solution. AgBF₄ (600 mg, 3 mmoles) was added and the mixture was stirred for 1 hour without heating. Ether (100 cm³) was added, the ethereal solution was washed with water, dried with MgSO₄, filtered and evaporated to produce 485 mg (70%) spectroscopically pure compound having formula 9 in the form of a white solid. Melting point 172°–174° C. (from hexane). $^1$H NMR (CDCl₃) δ 6.55 (1H); 3.8 (m, 3H); 2.85 (m, 4H); 2.4 (m, 2H); 2.1–1.2 (m, 22H). $^{13}$C NMR (CDCl₃): δ 171.5; 135.9; 130.3; 58.7; 53.9; 39.4; 39.0; 38.2; 37.6; 37.0; 35.3; 33.2; 32.1; 32.0; 31.7; 31.2; 30.5; 28.2; 27.2. IR (KBr): 3500, 2920, 1650, 1550, 1455, 1100 cm$^{-1}$. Mass: M⁺ at m/e 355 (100%); 266, 91, 73. Exact mass: calculated for $C_{23}H_{35}NO_2$: 355.251; found 355.249.

EXAMPLE VII

Figure 10:
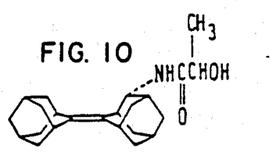
FIG. 10 illustrates the structural formula of N-(4-eq.-admantylideneadamantyl)lactamide.

Preparation of N-(4-eq.-adamantylidene adamantyl)-lactamide (formula 10)

The chloro-substituted compound having formula 2 (605 mg, 200 mmoles) and d,l-lactonitrile (9.2 g) were mixed under a nitrogen atmosphere, while AgBF₄ (600 mg, 3 mmoles) was added with stirring at 50° C. After 30 minutes, ether (110 cm³) was added. The ethereal solution was washed with water (8×100 cm³), dried with MgSO₄, filtered and evaporated to yield 440 mg (62%) of spectroscopically pure compound having formula 10 in the form of a white powder. $^1$H NMR (CDCl₃) δ 7.0 (br, 1H); 4.20 (q, J=13 c, 1H); 3.85 (m, 1H); 2.9 (m, 4H); δ 2.1–1.0 (m, 26H with doublet J=13 Hz at 1.40). $^{13}$C NMR (CDCl₃): δ 174.0; 173.96; 135.9; 130.4; 68.1; 53.4; 39.3; 39.0; 37.6; 37.0; 35.2; 33.1; 32.1; 32.0; 31.6; 31.2; 30.5; 30.4; 28.3; 28.2; 27.3; 21.0: IR (KBr): 3450, 2930, 1650, 1540, 1455, 1120 cm$^{-1}$. Mass: M⁺ at m/e 355 (100%); 267, 266, 91.79. Exact mass: calculated for $C_{23}H_{33}NO_2$ 355.251; found 355.249.

EXAMPLE VIII

Figures 11, 13:
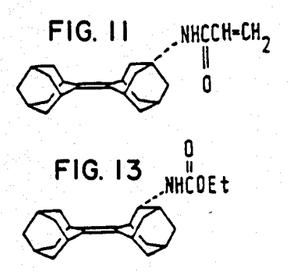
FIG. 11 illustrates the structural formula of N-(4-eq.-adamantylidene adamantyl)acrylamide.
FIG. 13 illustrates the structural formula of N-(4-eq.-adamantylideneadamantyl)ethyl carbamate.

Preparation of N-(4-eq.-adamantylidene adamantyl)acrylamide (formula 11)

To a stirred solution of the chloro-substituted compound having formula 2 (3.02 g, 10 mmoles), 100 mg hydroquinone, and 30 cm³ acrylonitrile in 80 cm³ dioxane, AgBF₄ (4.4 g) was added in 4 portions at 40° C. under a nitrogen atmosphere in the course of 2 hours. After this period a further quantity of 10 cm³ acrylonitrile was added to the yellow mixture, whereafter the whole was stirred at room temperature for 20 hours. The reaction mixture was filtered to remove precipitated AgCl, diluted with ether (200 cm³), washed with water, dried with MgSO₄, filtered and evaporated to yield 2.7 g of a yellowish solid. Column chromatography over Al₂O₃ using CH₂CL₂/benzene (1/1) as the eluent and recrystallization from MeOH produced 1.81 g (54%) pure compound having formula 11: melting point 190.5°–192° C. $^1$H NMR (CDCl₃): δ 6.20–6.08 and δ 5.6–5.4 (complex ABC systems and —NH absorption, 4H), 3.9 (m, 1H); 2.85 (m, 4H); 2.1–1.3 (m, 22H). $^{13}$C-NMR (CDCl₃): δ 164.6; 135.9 (s); 131.3 (d); 130.4 (s); 125.6 (t); 54.1; 39.4; 39.3; 38.9; 37.7; 37.0; 35.2; 33.1; 32.1; 32.0; 31.6; 31.2; 30.5; 28.3; 28.2; 27.3. IR (KBr): 3400, 2950, 660, 1630, 1535, 1460, 1220 cm$^{-1}$. Mass M⁺ at m/e 337 (100%); 266 with a meta-stability at 210; 213; 91, 79. Exact mass: calculated for $C_{23}H_{31}NO$: 337.241. Found: 337.243.

EXAMPLE IX

Figure 12:
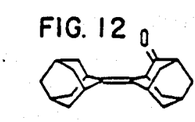
FIG. 12 illustrates the structural formula of adamantylideneadamantan-4-one.

Preparation of adamantylidene adamantan-4-one (formula 12)

A mixture of the chloro-substituted compound having formula 2 (10.1 g; 33 mmoles) and AgClO₄ (12 g) in 250 cm³ DMSO was heated at 150°–160° C. under a nitrogen atmosphere for 25 hours. After cooling and filtration, the product was extracted with n-hexane (4×15 moles). The hexane solution was washed with water, dried with MgSO₄, decolourized with 0.5 g activated charcoal, filtered and evaporated to produce 8.4 of the crude compound having formula 12. Chromatography over a short Al₂O₃ column, using CH₂Cl₂ as the eluent produced 7.15 g (76%) of the spectroscopically pure compound having formula 12 in the form of a white solid. All spectroscopic data were identical to those of the authentic sample. $^{13}$C NMR (CDCl₃): δ 215.5; 138.0; 129.2; 51.7; 46.2; 41.4; 39.2; 39.1; 38.1; 38.7; 38.3; 37.7; 36.6; 32.7; 31.8; 31.6; 30.7; 28.1; 27.9; 27.5.

EXAMPLE X

Preparation of N(4-eq.-adamantylidene adamantyl)ethylcarbamate (formula 13)

To a solution of 6.0 g (24 mmoles) AgBF₄ in 27 g ethylcarbamate, a solution of 6.05 g (20 mmoles) of the chloro-substituted compound having formula 2 in 250 cm³ of dioxane was added at 60° C. with stirring in the course of 15 minutes. The mixture was refluxed for a further period of 20 minutes, cooled, and concentrated at a reduced pressure. Ether (200 cm³) was added, the etheral solution was washed with water (3×200 cm³), dried with MgSO₄, filtered and evaporated. 100 cm³ iso-octane was added and evaporated, and this was repeated three times to removal residual quantities of ethylcarbamate. Column chromatography over Al₂O₃ (10 cm path, dia. 5 cm) using CHCl₃ as the eluent produced 6.54 g pure compound having formula 13 (87%) in the form of a white solid. Melting point 158°–159° C. (from EtOH/H₂O). $^1$H NMR (CDCl₃): δ 5.0/br, 1H); 4.1 (q, J=8 C, 2H); 3.65 (1H); 2.92 (m, 4H); 2.2–05 (25H) with triplet J=8 Hz at 1.27 ppm. $^{13}$C NMR (CDCl₃): δ 155.7; 135.8; 130.6; 60.3 (t); 55.4 (d); 39.4; 38.9; 37.7; 37.0; 35.7; 32.9; 32.1; 32.0; 31.1; 30.5; 28.3; 27.3; 14.4 IR (KBr): 3350, 2950, 1710, 1455, 1420, 1390, 1335 cm$^{-1}$. Mass: M+ at m/e 355 (100%); 267, 91.79. Exact mass: calculated for $C_{23}H_{33}NO_2$ 355.251. Found: 355.248.

EXAMPLE XI

Figure 14:
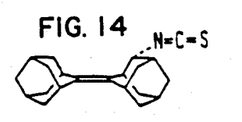
FIG. 14 illustrates the structural formula of 4-eq.-adamantylideneadamantane isothiocyanate.
Figure 15:
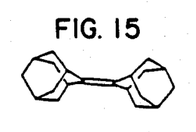
FIG. 15 illustrates the structural formula of adamantylideneadamantane.

Preparation of 4-eq.-adamantylidene adamantane isothiocyanate (formula 14)

To a solution of AgBF$_4$ (2.4 g, 12 mmoles) and freshly distilled benzylthiocyanate in 40 cm$^3$ dioxane, a solution of the chloro-substituted compound having formula 2 (2.42 g, 8 mmol) in 40 cm$^3$ dioxane was added with stirring over a period of 45 minutes. After being stirred for another hour, the mixture was concentrated at a reduced pressure. Ether was added, the solution washed with water, dried with MgSO$_4$, filtered, and evaporated at a greatly reduced pressure. Column chromatography over Al$_2$O$_3$, using CH$_2$Cl$_2$ as the eluent produced 1.6 g (61%) spectroscopically pure compound having formula 14 in the form of a white solid, melting point 180°–181° C. (from n-heptane). $^1$H-NMR (CDCl$_3$): δ 3.75 (br, 1H), 3.12 (br, 1H); 2.87 (br, 3H); 2.3–1.2 (m, 22H). $^{13}$C-NMR NMR (CDCl$_3$): 137.6; 129.7; 128.8; 62.5; 39.4; 38.7; 37.3; 36.9; 36.8; 33.0; 32.3; 32.2; 31.2; 30.3; 28.2; 27.2: Ir (KBr): 2940, 2200, 1460, 1345, 1085, 765 cm$^{-1}$. Mass: M+ at m/e 325, 267, 91, 79, 41. Exact mass: calculated 325.186. Found: 325.185.

EXAMPLE XII

Preparation of 4-eq.-chloroadamantylidene adamantane (Formula 2)

To a solution of 1 mmol (268 mg) adamantylidene adamantane having the formula 19 in 20 cm$^3$ CH$_2$Cl$_2$, 1.05 mmoles (140 mg) N-chlorosuccinimide was added. The reaction mixture was stirred at room temperature for 1 hour, diluted with CH$_2$Cl$_2$, and washed twice with water. The organic layer was dried with MgSO$_4$ and evaporated. The yield of 4-eq.-chloroadamantylideneadamantane was 300 mg (98%), melting point: 142°–143° C. (literature: 144°–145° C.). $^1$H NMR (CDCl$_3$): δ 4.15 (br s, 1H); 3.05 (br s 1H); 2.8 (br s, 3H); 2.6–1.15 (br m, 22H) ppm. When 0.1 mmol hydroquinone was added to the solution, exactly the same reaction occurred, and the product could be isolated in virtually the same quantitative yield.

EXAMPLE XIII

Figure 16:
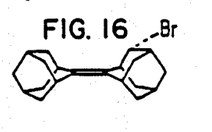
FIG. 16 illustrates the structural formula of 4-eq.-bromoadamantylideneadamantane.

Preparation of 4-eq.-bromoadamantylideneadamantane (formula 16)

To a solution of 3 mmols (804 mg) adamantylideneadamantane in 40 cm$^3$ CH$_2$Cl$_2$, 6.6 mmols (1.175 g) N-bromosuccinimide was added. The reaction mixture was refluxed and stirred for 12 hours. The reaction mixture was diluted with CH$_2$Cl$_2$ and washed twice with water and a saturated Na$_2$S$_3$O$_3$-solution. The organic layer was dried with MgSO$_4$ and evaporated. The yield of 4-eq.-bromoadamantylideneadamantane having formula 20 was 1.05 g (97%). An analytically pure sample could be obtained by crystallization from acetone and sublimation (115° C./0.002 mm); melting point 130.5–131.5° C. $^1$H NMR (CDCl$_3$); δ 4.4 (br s, 1H); 3.05 (br s, 1H); 2.8 (br s, 3H); 2.6–1.2 (br m, 22H); $^{13}$C NMR (CDCl$_3$); δ 136.9 (s); 131.0 (s); 63.8 (d) and 12 signals between 39.9 and 27.6. Analysis, calculated: 69.16 C; 7.84 H; 23.01 Br; found: 69.21 C; 7.82 H; 22.99 Br. Mass m/e 346:348 (1:1).

EXAMPLE XIV

Figure 18:
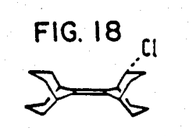
FIG. 18 illustrates the structural formula of 4-eq.-chlorobicyclo[3.3.1]nonylidene-bicyclo[3.3.1]nonane.

Preparation of 4-eq.-chlorobicyclo[3,3,1]-nonylidenebicyclo[3,3,1]nonane (formula 18)

Figure 17:
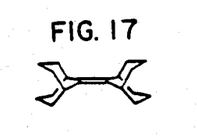
FIG. 17 illustrates the structural formula of bicyclo[3.3.1]-nonylidene-bicyclo[3.3.1]nonane.

To a solution of 200 mg (0.82 mmol) of bicyclo[3,3,1]nonylidene-bicyclo[3,3,1]nonane (formula 17) in 20 cm$^3$ CH$_2$Cl$_2$, 115 mg (0.86 mmol) N-chlorosuccinimide was added. The reaction mixture was refluxed and stirred for 1 hour, and CH$_2$Cl$_2$ was added to dilute the reaction mixture. The organic layer was washed twice with water, dried with MgSO$_4$ and evaporated. The yield of 4-eq.-chlorobicyclo[3,3,1]nonylidene-bicyclo[3,3,1]nonane was 190 mg. Purification was effected via chromatography (hexane, Al$_2$O$_3$) and sublimation (45° C./0.01 mm), melting point 50.53° C., $^1$H NMR (CDCl$_3$) δ 4.4–3.9 (m, 1H); 3.1 (br s, 1H): 2.85 (br s, 3H); 2.5–1.2 (br, 22H); $^{13}$C NMR (CDCl$_3$) δ 136.8 (s); 129.7 (s); 66.0 (d) and lines between 39.7 and 21.7; mass m/e 278:280 (3:1 ); exact mass: calculated 278.180; found 278.182.

EXAMPLE IV

Figure 19:
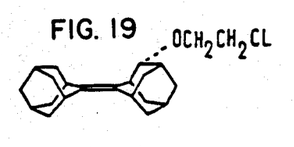
FIG. 19 illustrates the structural formula of 4-eq.-(2-chloroethoxy)adamantylideneadamantane.

Preparation of 4-eq.-(2-chloroethoxy)-adamantylideneadamantane (formula 19)

The bromo-substituted compound having formula 16 (220 mg, 0.58 mmol) was dissolved in dry dioxane (10 cm$^3$) and 2-chloroethanol (5 cm$^3$) was added. The mixture was refluxed for 18 hours, cooled, and concentrated at a reduced pressure. Water (50 cm$^3$) was added and the product was twice extracted with n-hexane, with the combined extracts being washed with brine. The hexane solution was dried with MgSO$_4$, filtered and concentrated at a reduced pressure. Columnchromatography over Al$_2$O$_3$ (act. II/III), using hexane as the eluent, produced 180 mg (0.52 mmol, 89.7%) of pure compound having formula 23 in the form of a colourless oil. IR (neat) 2950 (s), 1455 (m), 1100 (s) and 785 cm$^{-1}$ (s) $^1$H-NMR (CCl$_4$, TMS): δ 3.6 (double triplet, 4H), 3.25 (m, 1H), 2.85 (m, 5H), δ 2.4–1.1 (m, 22H), $^{13}$C-NMR (CBCl$_3$): δ 135.8; 130.8; 82.6 (d); 67.9 (t); 43.2 (t); 39.7; 39.6; 39.5; 39.1; 37.1; 36.8; 35.7; 33.0; 32.4; 32.1; 31.8; 31.0; 30.1; 28.4 and 27.6. Mass: M+ at m/e 346 (100%). Exact mass: calculated for $C_{22}H_{31}ClO$: 346.206. Found 346.205.

EXAMPLE XVI

Figure 20:
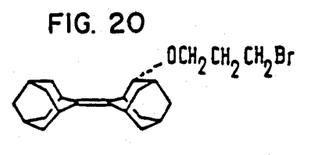
FIG. 20 illustrates the structural formula of 4-eq.-(3-bromopropyloxy)adamantylideneadamantane.

Preparation of 4-eq.-(3-bromopropyloxy)-adamantylideneadamantane (formula 20)

The bromo-substituted compound having formula 16 (200 mg, 0.58 mmol) was dissolved in dry dioxane (10 cm$^3$) and 3-bromopropanol-1 (5 cm$^3$) was added. The mixture was subsequently refluxed for 18 hours, and then concentrated at a reduced pressure. Water was added, and the product was extracted twice with n-hexane. The combined organic layers were washed with brine, dried with MgSO$_4$, filtered and evaporated substantially to dryness. Chromatography (see Example XV, the compound having formula 19) produced 195 mg (0.57 mmol, 85%) of the compound having formula 20 in the form of a colourless oil. IR (neat): 2900 (s), 1450 (m) and 1100 cm$^{-1}$ (s). $^1$H-NMR (CCl$_4$, TMS): δ 3.50 (t, J=6 Hz, 4H); 3.2 (m, 1H), 2.9 (m, 4H); 2.4–1.1 (m, 24H). $^{13}$C-NMR (CDCl$_3$): δ 135.6; 130.9; 82.0 (d);

68.2 (t); 64.6 (t); 39.7; 39.5; 39.4; 39.1; 37.2; 36.8; 35.7; 33.3; 33.0; 32.7; 32.3; 32.0; 31.7; 31.11; 31.08; 30.9; 30.4; 28.4; 27.6. Mass: M+ at m/e 404/406 (1-1; 100%). Exact mass: calculated for $C_{23}H_{33}BrO$: 404.172. Found 404.171.

EXAMPLE XVIII

Preparation of 4-eq.-(L)-menthoxy-adamantylideneadamantane (formula 21)

The bromo-substituted compound having formula 16 (200 mg, 0.58 mmol) was dissolbed in dry DMF (1' cm$^3$), and L-menthol (1 g, 5.8 mmol) was added. The mixture was refluxed for 18 hours and concentrated at a reduced pressure. Chromatography (following the procedure of Example XV, the compound having formula 19) produced the compound having formula 21 in the form of a colourless oil, yield 240 mg (98%). IR (neat): 2900 (s), 1450 (m), 1090 (s), 730 (s) cm$^{-1}$. $^1$H-NMR (CDCl$_3$, TMS): δ 3.6–2.8 (m, peaks at 3,5 and 3.0, 6H), 2.6–07 (m, 40H; peaks at δ 1.9, 1.0. 0.9 and 0.75). $^{13}$C-NMR (CDl$_3$): δ 135.22; 135.13; 131.86; 131.70; 80.1; 79.3; 78.2; 76.9; 49.1; 48.9; 42.0; 41.7 (all pairs of both diastereomeric isomers) and 26 peaks between δ 40 and 16. Mass: M+ peak at m/e 422.267 (100%), 283, 135. Exact mass: calculated for $C_{30}H_{46}O$ 422.355. Found: 422.357.

EXAMPLE XVIII

Preparation of 17β-[4-eq.-adamantylideneadamantyloxy-]-testosterone (formula 22)

The bromo-substituted compound having formula 16 (200 mg, 0.58 mmol) was dissolved in dry DMF (10 cm$^3$). Testosterone (1 g, 3.5 mmols) was added and the mixture was refluxed for 18 hours. Evaporation of the solvent, and columnchromatography (Al$_2$O$_3$), activity II/III, using CH$_2$Cl$_2$ as the eluent, produced 240 mg of crude product in the form of a yellow oil. The pure compound having formula 22 was obtained after plate chromatography (Al$_2$O$_3$/CH$_2$Cl$_2$) as a white solid. The yield was 100 mg (30%). $[α]_{478}^{rI} = +44.6$ (c=1.3; CH$_2$Cl$_2$). IR (KBr pellet): 2900 (s), 1680 (s), 1460 (m), 1090 (m) cm$^{-1}$. $^1$H-NMR (CDCl$_3$, TMS): δ 5.75 (br, 1H); 3.6–3.1 (m, 2H); 3.1–2.6 (m, 4H); 2.6–05 (m, 47H) with peaks at δ 1.8, 1.25, 1.2 and 0.85. $^{13}$C-NMR (CDCl$_3$): δ 199.2; 171.1 (s); 135.0 (s); 131.2 (s); 123.6 (d); 85.4; 85.2; 80.4; 80.3; 53.9; 50.4; 42.6 and 27 peaks between δ 40 and 11.5. Mass: M+ peak at m/e 554; 267 (100%). Exact mass calculated for $C_{29}H_{54}O_2$: 554.412. Found 554.411.

EXAMPLE XIX

Preparation of 4-eq.-[isopropyloxy-]-adamantylideneadamantane (formula 23)

The bromo-substituted compound having formula 16 (200 mg; 0.58 mmol) was dissolved in isopropanol (10 cm$^3$) and the solution was refluxed for 18 hours and subsequently evaporated to leave the compound having formula 23 in the form of a colourless oil (0.55 mmol, 95%). IR (neat): 2900 (s), 1450 (m), 1080 (s) cm$^{-1}$. $^1$H-NMR (CCl$_4$, TMS): δ3.6 (septet, J=7C, 1H), 3.25 (m, 1H); 2.9 (m, 4H) and 2.5–1.0 (m, 28H with sharp doublet at δ1.15, J=6C). $^{13}$C-NMR (CDCl$_3$): δ135.2; 131.4; 78.7; 67.4; 39.7; 39.6; 39.5; 39.4; 39.2; 37.2; 37.1; 36.1; 33.0; 32.5; 32.3; 32.1; 31.2; 31.0; 28.4; 27.2; 22.8; 22.6. Mass: M+ peak at m/e 326 (100%); 268, 266; 135. Exact mass: calculated for $C_{23}H_{34}O$: 326.261. Found 326.263.

EXAMPLE XX

Preparation of 4-eq.-[3-hydroxypropyloxy-]-adamantylidene adamantane (formula 24)

The bromo-substituted compound having formula 16 (200 mg, 0.58 mmol), dioxane (10 cm$^3$) and propanediol-1.3 (5 cm$^3$) were mixed, and refluxed for 18 hours. Dioxane was evaporated, and the residue dissolved in CH$_2$Cl$_2$ (50 cm$^3$). The solution was treated with H$_2$O (3×50 cm$^3$), dried with MgSO$_4$, filtered, and evaporated to produce 180 mg (91%) spectroscopically pure compound having formula 24 in the form of a colourless oil. Analytically pure material was obtained after "Kugelrohr"to distillation (250° C., 0.002 mm Hg). Analysis: calculated for $C_{23}H_{34}O_2$: 80.63% C 10.02% H. Found 80.52% C 9.95% H. IR (neat): 3400 (s), 2900 (s), 1450 (s), 1100 (br) cm$^{-1}$. $^1$H-NMR (CCl$_4$, TMS): δ3.6 (t, J=7C, 2H), 3.5 (t, J=7C, 2H); 3.2 (br, 1H); 2.9 (br, 4H); 2.3–1.0 (m, 25H). $^{13}$C-NMR (CDCl$_3$): δ135.4; 130.5; 82.1 (d); 66.6 (t); 61.8 (t); 39.2; 38.8; 36.9; 36.5; 35.2; 32.8; 32.0; 31.7; 31.3; 30.8; 30.6; 28.1; 27.3. Mass: M+ peak m/e 342 (100%); 267; 135; 79.

EXAMPLE XXI

Preparation of 4-eq.-hydroxy-adamantylidene adamantane (formula 3)

The bromo-substituted compound having formula 16 (347 mg, 1 mmol) was dissolved in dioxane (15 cm$^3$) and H$_2$O (5 cm$^3$) was added. After refluxing for 0.5 hour, the solvents were removed by evaporation, and CH$_2$Cl$_2$ (100 cm$^3$) was added. After treating this solution with H$_2$O (2×100 cm$^3$) MgSO$_4$ was added, the solution was filtered and evaporated to produce the compound having formula 3 (280 mg, 99%) in the form of a white amorphous powder, melting point 211.5°–213° C.

EXAMPLE XXII

Preparation of 4-eq.-acetoxy-adamantylidene-adamantane (formula 25)

A solution of the bromo-substituted compound having formula 16 (200 mg, 0.58 mmol) in acetic acid (10 cm$^3$) was refluxed for 36 hours. Evaporation of the solvent and fast chromatography over a short column of Al$_2$O$_3$ (activity II/III), using n-hexane as the first eluent and then CH$_2$Cl$_2$, produced the compound having formula 25 (140 mg, 74%) in the form or a colourless oil, which after standing for 1 day solidified. IR (neat): 2950 (s), 1715 (s), 1220 (s) cm$^{-1}$. $^1$H-NMR (CDCl$_3$, TMS): δ4.7 (br, 1H); 3.1–2.6 (br, 4H); 2.2–1.2 (m, 25H; with a peak at 2.05 for —CH$_3$). $^{13}$C-NMR (CDCl$_3$): δ170.4; 136.7; 129.8; 77.1; 39.6; 39.5; 39.4; 39.0; 37.1; 36.9; 36.7; 35.6; 33.3; 32.4; 32.2; 31.6; 31.3; 30.6; 28.4; 28.3; 27.4; 21.4. Mass: M+ peak at m/e 326. Exact mass: calculated for $C_{22}H_{30}O_2$ 326.22. Found 326.226.

EXAMPLE XXIII

Preparation of N-(4-eq.-adamantylidene adamantyl-)-3-hydroxypropionamide (formula 26)

A mixture of the bromo-substituted compound having formula 16 (200 mg, 0.58 mmol), dioxane (10 cm$^3$) and cyanohydrine (5 cm$^3$) was concentrated at a reduced pressure, and dissolved in ether (50 cm$^3$). The ethereal solution was washed with H$_2$O (2×50 cm$^3$) and brine (1×50 cm$^3$), dried with MgSO$_4$, filtered, and evaporated to produce 100 mg (49%) of pure compound having formula 26 in the form of a white solid. Melting point: 172°-174° C. (from hexane). IR (KBr pellet): 3300 (m, br), 2900 (s), 1640 (s), 1540 (m), 1450 (m) cm$^{-1}$. $^1$H-NMR, $^{13}$C-NMR and mass identical to the reaction with Ag$^{30}$.

EXAMPLE XXIV

Preparation of 4 eq.-iodo-adamantylidene admantane (formula 27)

The bromo-substituted compound having formula 16 (347 mg, 1 mmol) was added to a solution of NaJ (4.5 g) in acetone (25 cm$^3$), and the whole was then refluxed for 20 hours. The solvent was evaporated, ether (50 cm$^3$) was added, whereafter the solution was treated with water (2×50 cm$^3$), concentrated Na$_2$S$_2$O$_3$ (1×50 cm$^3$) and water (1×50 cm$^3$). The ethereal solution was dried with MgSO$_4$, filtered and evaporated to produce 340 mg (86%) of pure compound having formula 27 in the form of a white solid. IR (KBr pellet): 2950 (s), 1450 (s), 1145 (m), 965 (m), 750 (m) cm$^{-1}$. $^1$H-NMR (CDCl$_3$, TMS): δ3.2-2.7 (m, 4H); 2.7-1.0 (m, 22H). $^{13}$C-NMR (CDCl$_3$): δ136.6; 131.2; 47.3; 41.1; 40.1; 39.5; 39.3; 37.5; 36.9; 34.3; 32.6; 32.3; 32.1; 30.7; 28.2; 27.9. Mass: M+ peak at m/e 394; 267 (100%). Exact mass: calculated for C$_{20}$H$_{27}$I: 394.116. Found 394.114.

EXAMPLE XXV

Preparation of 4-eq.-bromo-2,2'-epidioxy-2,2'-adamantyl adamantane

The bromo-substituted compound having formula 16 (1,5 mmol) was dissolved together with a pinch (approximately 12 mg) of methylene blue in 200 cm$^3$ of distilled CH$_2$Cl$_2$. This solution was transferred to a reactor which was made mainly of glass.

In the reaction vessel, a porous P-4 glass filter is provided. Placed on reaction vessel is a spherical cooler with a superjacent glass tube, approximately 1 m long. Placed on top of the reaction vessel is further a supply vessel for the solvent (in this case CH$_2$Cl$_2$).

Before the solution was transferred to the reaction vessel, oxygen (O$_2$) was passed through the reaction vessel. When the solution was added to the reaction vessel, this oxygen stream became visible from the rising in the solution of finely divided bubbles.

The solution present in the reaction vessel was irradiated with the sodium vapour lamp and the reflector, placed close to the reaction vessel, for 6 hours, with the liquid level being replenished from time to time with CH$_2$Cl$_2$ from the supply vessel. During the reaction the temperature of the solution rose to approximately 40° C. The course of the reaction was followed by means of thin-layer chromatography (aluminum oxide/CH$_2$Cl$_2$ or n-hexane).

After completion of the reaction, the solution was poured out and decolorized with activated charcoal. The reaction product was purified by column chromatography to product 4-eq.-bromo-2,2'-epidioxy-2,2'-adamantyl adamantane.

EXAMPLE XXVI

Figure 32:
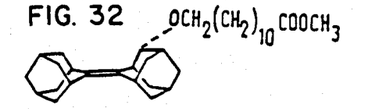
FIG. 32 illustrates the structural formula of 4-eq.-[12-oxydodecanoic acid methyl ester[adamantylideneadamantane.

Preparation of 4-eq.-[12-oxy-dodecanoic acid methyl ester]-adamantylidene adamantane (formula 32)

To a solution of 10 g 12-hydroxydodecanoic acid methyl ester having the formula 35 and 7 g AgClO$_4$ in 200 cm$^3$ 1.4-dioxane, a solution of 5 g 4-eq.-chloroadamantylidene adamantane (formula 2) in 100 cm$^3$ dry 1.4-dioxane was added. The reaction mixture was stirred at room temperature for 40 hours, and subsequently poured into 500 cm$^3$ water and extracted with ether (3×200 cm$^3$). The combined organic layers were washed with water (7×150 cm$^3$), dried by means of MgSO$_4$, and evaporated, to produce 14.5 g crude mixture. The excess of compound having formula 35 was removed by means of column chromatography (Al$_2$O$_3$ act. II/III; CH$_2$Cl$_2$). Three crystallizations from methanol produced 2.98 g of the compound having formula 32. Gas chromatographic analysis showed, however, that approximately 15% dodecane lactone (formula 36) was present.

A suitable way of purifying the compound having formula 32 comprised the following procedure: the crude mixture was, after column chromatography (see supra), dissolved in 250 cm$^3$ methanol together with 0.5 g p-toluenesulphonic acid, and refluxed for 14 hours. After cooling the solvent was evaporated and the reaction mixture chromatographed over an Al$_2$O$_3$ (II, II), CH$_2$Cl$_2$ column to produce a mixture of the compound having formula 32 and 4-eq.-methoxyadamantylidene adamantane (formula 5). The latter compound was removed by hydrolysis of the compound having formula 32 with 2 g LiOH in ethanol, water (10:10 cm$^3$) at room temperature for 12 hours, followed by column chromatography (Al$_2$O$_3$ II, III; CH$_2$Cl$_2$) which produced the 4-eq.-methoxy compound. The pure compound having formula 32 was isolated by Soxhlet extraction of the column chromatography material with 300 cm$^3$ methanol containing 0.5 g p-toluenesulphonic acid, followed by column chromatography (Al$_2$O$_3$ II, III, CH$_2$Cl$_2$). An analytically pure sample of the compound having formula 32 was obtained by crystallization from methanol: melting point 44°-48° C., IR(Nujol): 2900, 1740, 1470, 1390, 1100 cm$^{-1}$; 1H-NMR (CDCl$_3$) δ3.68 (s. 3H); 3.56-31. (br. 3H); 3.1-2.7 (br. 4H); 2.5-2.1 (br. 2H); 2.1-1.5 (br. adamantane); 1.5-1.15 (br. CH$_2$ chain). $^{13}$C-NMR (CDCl$_3$): δ174.2; 135.3; 131.2; 81.7; 67.4; 51.3 and 21 lines between 39.5-24.8. Mass spectrum m/e calc.: 496, 392; found 496, 393. Analysis: calc.: 79.79 C; 10.55 H; found: 79.87 C; 10.47 H.

EXAMPLE XXVII

Preparation of SYN and ANTI 4-eq.-[12-oxy-dodecanoic acid methyl ester]-adamantylidene-adamantane-1,2-dioxetane (formula 33)

A solution of 240 mg of the compound having formula 32 and 15 mg methylene blue in 200 cm$^3$ CH$_2$Cl$_2$ was irradiated with a high-pressure mercury lamp, while a slow stream of oxygen was passed through the solution. The UV light was filtered with a K$_2$Cr$_2$O$_7$ solution. The reaction was followed by gas chromatographic analysis. A reaction period of 7 hours was required for complete conversion of the olefin in the 1,2-dioxetane having formula 33. The dichloromethane was evaporated from the reaction mixture, which was then purified over an Al$_2$O$_3$ (II, III) column with CH$_2$Cl$_2$.

The yield of compound having formula 33 in the form of a colourless oil was 240 mg (94%): IR neat: 2900, 1715, 1460 and 1100 cm$^{-1}$; $^1$H NMR (CDCl$_3$): $\delta$3.60 (S 3H); 3.6-3.2 (br.m., 3H); 2.8-2.4 (br.m., 4H); 2.4-1.0 (br.m., 42H); $^{13}$C NMR (CDCl$_3$): $\delta$174.1 (s); 96.4 (s); 960 (s); 95.6 (s); 95.5 (s); 76.0 (d); 67.9 (d); 67.7; 51.2 (q) and 24 lines between 37.0 and 24.8 ppm.

EXAMPLE XXVIII

Preparation of SYN and ANTI 4-eq.-[12-oxy-dodecanoic acid]adamantylidene-adamantane-1,2-dioxetane (formula 34)

To a solution of 240 mg of the compound having formula 33 in 15 cm$^3$ ethanol, a solution of 250 mg LiOH in 3 cm$^3$ water was added. The reaction mixture was stirred at room temperature for 12 hours. After acidification (pH=4) with 0.1N H$_2$SO$_4$, the reaction mixture was extracted with CH$_2$Cl$_2$ (2×30 cm$^3$). The organic layer was dried by means of MgSO$_4$, and concentrated. The yield of compound having formula 34 in the form of a colourless oil was 216 mg (92%): IR neat: 2900, 2500-3500, 1700, 1460, 1260, 1220 cm$^{-1}$; $^1$H NMR (CDCl$_3$) $\delta$10.2-9.9 (s, 1H); 3.7-3.2 (br. m., 3H); 2.9-2.4 (br. m., 4H); (br. m., 42H); $^{13}$C NMR (CDCl$_3$): $\delta$179.7 (s); 95.8 (s); 95.4 (s); 95.3 (s); 75.9 (d); 75.7 (d); 67.8 (d); 67.5 (d) and 25 lines between 37.0 and 24.4 ppm.

EXAMPLE XXIX

Preparation of 3-O-(4-eq.-adamantylidene-adamantyl)-lithocholic acid methyl ester (formula 38)

To a stirred solution of 8 g of the compound having formula 37 and 3.5 g 4-eq.-chloroadamantylidene adamantane (formula 2) in 250 cm$^3$ p-dioxane under a nitrogen atmosphere, 4.4 g AgBF$_4$ was added. The reaction mixture was stirred at room temperature for 15 hours and diluted with ether. The organic layer was washed with water (six times), dried by means of MgSO$_4$, and concentrated. The crude product was thoroughly washed with methanol to remove the starting materials. The yield of compound having formula 38 was 4.5 g (95%). An analytically pure sample was obtained by crystallization from CH$_2$Cl$_2$/iso-propyl alcohol; melting point: 162.5°-164° C.; IR (Nujol): 1740, 1289, 1095 cm$^{-1}$; $^1$H NMR (CDCl$_3$): $\delta$3.57 (s, 3H); 3.45-3.2 (br.m., 2H); 3.0-2.6 (br.m. 4H); 2.4-04 (br.m., 53H); 0.84 (s, 3H), 0.55 (s, 3H); $^{13}$C NMR (CHCl$_3$): $\delta$174.0 (s); 134.9 (s); 131.2 (s); 78.2 (d), 75.2 (d), 56.1 (d), 55.7 (d); 50.9 (q) and 29 lines between 42.3 and 11.7 ppm; analysis C$_{45}$H$_{68}$O$_3$: calc.: 82.26% C; 10.43% H; found: 82.06% C; 10.44% H.

EXAMPLE XXX

Preparation of 3-O-(4-eq.-2,2'-epidioxy-2,2'-adamantyl adamantane)lithocholic acid methyl ester (formula 39)

A solution of 2.5 g of the compund having formula 38 and 50 mg methylene blue in approximately 350 cm$^3$ CH$_2$Cl$_2$ was irradiated with a high-pressure mercury lamp, while a slow stream of oxygen was passed through the solution. The UV light was filtered by means of a K$_2$CR$_2$O$_7$ solution. Complete conversion required a reaction period of 20 hours The solvent was evaporated from the reaction mixture, and the residue was purified over an Al$_2$O$_3$ (act. II/III) column with CH$_2$Cl$_2$. The yield of compound having formula 39, in the form of white crystals, was 2.0 g (76%). An analytically pure sample was obtained by crystallization from iso-propylalcohol; melting point: 119°-121° C.; IR (nujol) 1740; 1160; 1100 cm$^{-1}$; $^1$H NMR (CDCl$_3$) $\delta$3.7-3.4 (br.m., 1H); 3.54 (s, 3H); 3.4-3.0 (br.m. 1H); 2.7-2.3 (br.m. 4H); 2.3-0.4 (br.m. 53H); 0.77 (s, 3H); $^{13}$C NMR (CDCl$_3$): $\delta$174.0 (s), 96.0 (s), 95.5 (s); 95.2 (s); 94.9 (s); 75.7 (d); 75.3 (d); 72.6 (d), 56.0 (d), 50.9 (q) and 28 lines between 42.3 and 11.6 ppm.; analysis C$_{45}$H$_{68}$O$_5$ calc.: 78.44%; 9.95% H; found 78.26% C; 9.99% H.

EXAMPLE XXXI

Preparation of 3-O-(4-eq.-2,2'-epidioxy-2,2'-adamantyladamantane)- lithocholic acid (formula 31)

To a solution of 200 mg of the compound having formula 39 in 25 cm$^3$ ethanol, 350 mg LiOH in 5 cm$^3$ water was added. The reaction mixture was stirred at room temperature for 12 hours. After acidification (pH=4) with 0.1N H$_2$SO$_4$, the reaction mixture was extracted with CH$_2$Cl$_2$. The organic layer was dried by means of MgSO$_4$ and concentrated. The yield of compound having formula 31 in the form of white crystals was 192 mg (98%): melting point: 138°-140° C.; IR (Nujol): 3700-2700; 1705, 1090 cm$^{-1}$; $^1$H NMR (CDCl$_3$) $\delta$3.8-3.3 (br.m, 1H); 3.6-3.0 (br.m. 1H); 2.8-2.3 (br.m., 4H); 2.5-94 (br.m., 53H); 0.8 (s, 3H); 0.55 (s., 3H) and 10.1-10.7 (br.s., 1H); $^{13}$C NMR (CDCl$_3$): $\delta$180.3 (s); 96.4 (s); 59.9 (s); 95.7 (s); 95.5 (s); 75.7 (d); 75.4 (d); 72.9 (d); 56.2 (d); 55.8 (d) and 34 lines between 42.5 and 11.9 ppm.

EXAMPLE XXXII

Preparation of N-(4-eq.-adamantylidene adamantyl)-maleimide (formula 40)

Under a dry nitrogen atmosphere and with exclusion of light, a mixture of 6.05 g 4-eq.-chloroadamantylidene adamantane (formula 2), 200 cm$^3$ dry toluene, 20 mg hydroquinone and 5.2 g silver maleimide (formula 41) (from silver nitrate and maleimide) was boiled for 27 hours. After evaporation and addition of 100 cm$^3$ ether, a mixture of solids was obtained. Extraction by means of a Soxhlet apparatus, using ether as the solvent for 18 hours, and evaporation of the extract produced 6.0 g yellowish solid. Column chromatography over Al$_2$O$_3$ (act. II/III) with benzene as the eluent, evaporation and water with 20 cm$^3$ ether gave 2.7 g (37%) pure maleimide; melting point: 199°-202° C. $^1$H-NMR (CDCl$_3$, TMS): $\delta$6.52 (s, 2H); 3.9 (m, 1H); 3.5 (m, 2H); 2.9 (m, 4H); 2.7-1.0 (m, 20H). $^{13}$C NMR (CDCl$_3$): $\delta$171.9; 135.9; 133.8; 130.9; 61.5; 39.4; 39.0; 37.1; 34.0; 32.3; 32.1; 31.9; 31.0; 30.2; 28.3; 26.9. IR (KBr): 2900 (s), 1700 (s), 1340 (m) cm$^{-1}$. Mass: M$^+$ peak at 363. Exact mass: calc. 363.220. Found: 363.222.

EXAMPLE XXXIII

Preparation of 4-eq.-(maleimido)-2,2'-epidioxy-2,2'-adamantyl adamantane (2-isomers)

The olefin having formula 40 (500 mg) was subjected to photooxygenation in the manner specified before, except that the reaction period was 18 hours. Column chromatography over Al$_2$O$_3$ (act. III), using benzene as the eluent gave after a first fast travelling impurity the isomer having the formula 42a (75 mg) in the pure form and thereafter the isomer having formula 42b (60 mg) in the pure form, and both as white solids (together 25% yield).

Formula 42a:

$^1$H-NMR (CDCl$_3$, TSM): δ6.5 (s, 2H), 4.2 (m. 1H), 3.4 (m, 1H), 2.9–2.5 (m, 4H), 2.4–1.0 (m, 21H). IR (KBr): 2950 (s), 1700 (s), 1365 (m), 1345 (m), 685 (m) cm$^{-1}$. $^{13}$C-NMR (CDCl$_3$): δ171.7; 133.9; 95.8; 55.8; 37.1; 35.2; 34.4; 33.9; 33.0; 32.2; 31.9; 31.3; 30.9; 29.5; 27.2; 26.5; 26.3; 24.9.

Formula 42b:

$^1$H-NMR (CDCl$_3$, TMS): δ6.55 (s, 2H), 4.15 (m, 1H), 3.4 (m, 1H), 2.9–2.4 (m, 4H), 2.4–1.0 (m, 21H). IR (KBr): 2900 (s), 1700 (s); 1375 (m), 690 (m) cm$^{-1}$. $^{13}$C-NMR (CDCl$_3$): δ171.7; 133.9; 95.9; 55.3; 37.1; 34.5; 34.1; 33.7; 32.6; 31.9; 31.7; 31.5; 31.4; 31.1; 29.6; 28.8; 26.5; 26.3; 25.1.

EXAMPLE XXXIV

Preparation of 4-eq.-(α-iodoacetoxy)-2,2'-epidioxy-2,2'-adamantyl adamantane (formula 29) ("anti-isomer")

200 mg of the compound having formula 43, 284 mg pro-analysis iodo acetic acid and 150 mg pro-analysis pyridine were together dissolved in 30 cm$^3$ distilled CH$_2$Cl$_2$. After the solution had been cooled to 0° C., brought under a nitrogen atmosphere, and sealed from light, a solution of 330 mg DCC (dicyclohexylcarbodiimide) in 2 cm$^3$ CH$_2$Cl$_2$ was injected by means of a glass syringe with stirring. Without further cooling, the mixture was stirred for three days. After evaporation, 50 cm$^3$ benzene was added, the solution was filtered and the residue washed with benzene. The combined benzene solutions were washed with 5% Na$_2$S$_2$O$_3$ solution (2×50 cm$^3$) and H$_2$O (1×50 cm$^3$), dried by means of MgSO$_4$, filtered, and evaporated. The yellow solid residue was dissolved in pro-analysis acetone and the solution was partially decolorized by means of decolorizing charcoal. After filtration, the solution was thickened to about 25 cm$^3$ volume, subsequently a little water was added, the solution was filtered and then allowed to stand for 18 hours at −40° C. for crystallization. Filtration and drying produced 140 mg pure product (42%); melting point 137.2°–137.9° C. $^1$H-NMR (CDCl$_3$, TMS): δ5.15 (br, 1H); 3.75 (s, 2H): 3.1–2.4 (m, 4H); 2.4–1.1 (m, 22H). IR (KBr): 2900 (s), 1720 (s) and 1265 (s) cm$^{-1}$. $^{13}$C-NMR (CDCl$_3$): δ167.9; 95.6; 95.2; 74.1; 36.9; 35.8; 34.7; 34.3; 32.9; 32.0; 31.8; 31.5; 31.4; 30.9; 30.5; 30.1; 26.5; 26.3; 25.3; −5.1.

The reaction to form 4-eq.-(α-iodoacetoxy)-2,2'-epidioxy-2,2'-adamantyl adamantane (formula 29) can also be carried out on a mixture of syn and anti hydroxydiadamantyl-1,2-dioxetane. There is then formed a mixture of syn and anti α-iodoacetoxy compounds in the same yield. The I.R.- and the $^1$H-NMR-spectra are identical to those of the pure anti-isomer. $^{13}$C-NMR(CDCl$_3$): δ167.9; 167.5; 95.5; 95.7; 95.2; 74.3; 74.1 and 27 peaks between 39.1 and 25; −41.9 and −5.1.

The syn- and anti-4-eq.-hydroxy-1,2-dioxetanes needed for the above synthesis, can be prepared from 4-eq.-hydroxyadamantylidene adamantane via the photo-oxygenation method in a quantitative yield (after purification by column chromatography over Al$_2$O$_3$ (act. II/III) using ether as the eluent. The separation of syn- and anti-isomers is effected by means of plate chromatography with Al$_2$O$_3$ and CH$_2$Cl$_2$ as the eluent.

We claim:

1. A process for preparing a 4-equatorially halogen-substituted polycyclo-alkylidene polycyclo-alkane, comprising halogenating, in a solvent, the corresponding nonsubstituted polycyclo-alkylidene polycycloalkane compound with a halogenating agent of the class consisting of N-halosuccinimide, tert.-butyl-hypohalite and sodium hypohalite/CH$_3$COOH.

2. The process of claim 1 wherein said halogen is chlorine and, corresponding, said halogen-substituted polycycloalkylidene polycyclo-alkane is a chlorine-substituted polycycloalkylidene polycyclo-alkane.

3. The process of claim 2, further comprising the step of substituting, in a solvent and in the presence of a silver salt, said chlorine using, as substituting agent, a nucleophile.

4. The process of claim 3, wherein said silver salt is selected from the group consisting of AgBF$_4$ or AgClO$_4$.

5. The process of claim 1, wherein said halogen is bromine.

6. The process of claim 5, further comprising the step of substituting, in a solvent, in the absence of a silver salt, said bromine using, as substituting agent, a nucleophile, and wherein said solvent comprises said nucleophile.

7. The process of claim 6, wherein said solvent further comprises a co-solvent selected from the group consisting of dimethylformamide and dioxane.

8. The process of claim 5 wherein the product of said halogenation is subjected to a halogen-exchange reaction.

9. The process of claim 8, wherein said halogen-exchange reaction is carried out with NaI/acetone mixture to form the corresponding iodo-substituted compound.

10. The process of claim 1 wherein said polycycloalkylidene polycyclo-alkane is adamantylidene adamantane.

11. A process for preparing a 4-equatorially substituted epidioxy polycyclo-alkylidene polycyclo alkane, comprising subjecting a compound selected from the group consisting of:

A. 4-equatorially-halogen-substituted polycycloalkylidene polycyclo-alkane formed by halogenating, in a solvent, the corresponding non-substituted polycyclo-alkylidene polycyclo-alkanes with a halogenating agent of the class consisting of N-halosuccinimide, tert.-butyl-hypohalite, and sodium hypohalite/CH$_3$COOH, and

B. The compounds resulting from substituting said halogen in said 4-equatorially-halogen-substituted polycyclo-alkylidene polycyclo-alkanes with a nucleophile, to a photo-oxygenation reaction.

12. The process of claim 11, wherein said non-substituted polycyclo-alkylidene polycyclo-alkane is adamantylidene adamantane and, corresponding, said substituted-epidioxy polycyclo-alkylidene polycycloalkane is a 4-eq.-substituted-2,2'-epidioxy-2,2'-adamantyl adamantane.

13. The process of claim 12, wherein a CH$_2$Cl$_2$ solution of methyleneblue and 4-eq.-substituted adamantylidene adamantane is subjected to a photo-oxygenation reaction in a reaction vessel through which oxygen is passed, and with irradiation for 4–7 hours with a sodium lamp, followed by decolorizing the reaction solution with activated charcoal, purifying said product with column chromatography, and recovering said product.

14. A compound having the formula wherein
A and B are alkylene radicals, optionally connected to each other through an alkylene radical; and
R₁ is a substituent, provided that R₁ is not chloro, hydroxy, oxo, D or a group having the formula when said compound is 4-eq.-R₁-2,2'-admantylidene adamantane.

15. The compound of claim 14, wherein said alkylene radical A contains 2 to 5 carbon atoms, said alkylene radical B contains 2 to 5 carbon atoms, and said connecting alkylene radical contains 1 to 4 carbon atoms.

16. The compound of claim 14, wherein said compound is 4-eq.-R₁-2,2'-admantylidene adamantane, provided that R₁ is not chloro, hydroxy, oxo, D or a radical having the formula 17. The compound of claim 14, wherein R₁ is selected from the group consisting of
chloro, bromo, iodo,
hydroxy,
substituted or unsubstituted alkoxy, cycloalkoxy, acyloxy, and
amino, acylamino, isothiocyanato, and isocyanato, provided that if said compound is 4-eq.-R₁-2,2'-adamantylidene adamantane, R₁ cannot be chloro, hydroxy, oxo, D, or a group having the formula 18. A compound having the formula wherein
A and B are alkylene radicals, optionally connected to each other through an alkylene radical; and
R₁ is selected from the group consisting of an acyloxy group comprising a protein radical, a cycloalkoxy comprising a steroid radical attached through an oxygen, an acyloxy comprising a fatty acid radical attached through an oxygen.

19. The compound of claim 18, wherein R₁ is an acyloxy group, comprising a protein radical.

20. The compound of claim 19, wherein said protein radical is a radical of bovine serum albumin.

21. The compound of claim 18, wherein R₁, as cycloalkoxy, is a steroid radical attached through an oxygen atom.

22. The compound of claim 21 wherein said steroid radical is selected from the group consisting of testosterone and lithocholic acid radicals.

23. The compound of claim 18, wherein R₁, as acyloxy, is a fatty acid radical attached through an oxygen atom.

24. The compound of claim 23, where said fatty acid radical is a radical of arachidic acid.

25. A chemiluminescent label comprising a compound having the formula wherein
A and B represent alkylene radicals, optionally connected to each other through an alkylene radical, and
R₂ is a substitutent,
provided that said substituent is not chloro or hydroxy when said chemiluminescent compound is 4-eq.-R₂-2,2'-epidioxy-2,2'-adamantyl adamantane.

26. The chemiluminescent label of claim 25, wherein said optionally connected alkylene radicals A and B contain 2 to 5 carbon atoms, and
said connecting alkylene radical contains 1 to 4 carbon atoms.

27. The chemiluminescent label of claim 25, wherein said compound is 4-eq.-R₂-2,2'-epidioxy-2,2'-adamantyl admantane, provided that R₂ is not chloro or hydroxy.

28. The chemiluminescent label of claim 25, wherein R₂ is selected from the group consisting of
chloro, bromo, iodo,
hydroxy,
substituted or unsubstituted alkoxy, cycloalkoxy, or acyloxy,
amino, acylamino, isothiocyanato and isocyanato, provided that R₂ is not chloro or hydroxy when said compound is 4-eq.-R₂-2,2'-epidioxy-2,2'-adamantyl adamantane.

29. The chemiluminescent label of claim 28, wherein R₂ is an acyloxy group comprising a protein radical.

30. The chemiluminescent label of claim 29, wherein said protein radical is a radical of bovine serum albumin.

31. The chemiluminescent label of claim 28, wherein R₂, as cycloalkoxy, is a steroid radical attached through an oxygen atom.

32. The chemiluminescent label of claim 31, wherein said steroid radical is selected from the group consisting of testosterone and lithocholic acid radicals.

33. The chemiluminescent label of claim 28, wherein R₂, as acyloxy, is a fatty acid radical attached through an oxygen atom.

34. The chemiluminescent label of claim 33 wherein said fatty acid radical is an arachidic acid radical.

* * * * *